United States Patent [19]
Sakurai et al.

[11] Patent Number: 5,831,125
[45] Date of Patent: Nov. 3, 1998

[54] METHOD OF MAKING PRIMARY AMIDE DERIVATIVE

[75] Inventors: Kazutoshi Sakurai; Kenya Ishida; Miharu Ogura, all of Kanagawa, Japan

[73] Assignee: Takasago International Corporation, Tokyo, Japan

[21] Appl. No.: 843,838

[22] Filed: Apr. 17, 1997

[30] Foreign Application Priority Data

Oct. 11, 1996 [JP] Japan .................................. 8-287350

[51] Int. Cl.⁶ ...................... C07C 231/08; C07C 231/10
[52] U.S. Cl. ........................................... 564/135; 564/136
[58] Field of Search ..................... 564/135, 136

[56] References Cited

U.S. PATENT DOCUMENTS

| | | | |
|---|---|---|---|
| 5,198,210 | 3/1993 | Critchley | 424/78.03 |
| 5,326,565 | 7/1994 | Critchley | 424/401 |

FOREIGN PATENT DOCUMENTS

| | | |
|---|---|---|
| 63-216852 | 9/1988 | Japan . |
| 4282304 | 10/1992 | Japan . |
| 7505163 | 6/1995 | Japan . |
| 93 20038 | 10/1993 | WIPO . |

OTHER PUBLICATIONS

CAPLUS, 1992:214015, Frings, abstract of DE 4042386, Feb. 22, 1992.

The Journal of The American Oil Chemists' Society: vol. 38, pp. 600–605 (1961).

Journal of American Chemical Society; vol. 80, pp. 2170–2171 (1958).

*Primary Examiner*—John Kight
*Assistant Examiner*—D. Margaret M. Mach
*Attorney, Agent, or Firm*—Sughrue, Mion, Zinn, Macpeak & Seas, PLLC

[57] ABSTRACT

A method of selective N-acylation of an aminodiol having a primary alcoholic hydroxyl group and a secondary alcoholic hydroxyl group, in which the objective product can be prepared in high yield and without troublesome extraction and purification operations. More particularly, a method of making a primary amide derivative represented by the following general formula (3) is disclosed:

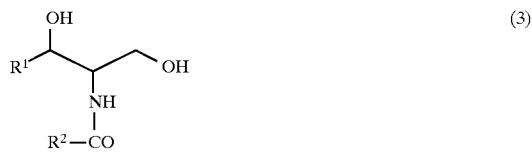

(3)

wherein $R^1$ represents a linear saturated aliphatic hydrocarbon group having 11 to 19 carbon atoms, $R^2$ represents a linear saturated or unsaturated aliphatic hydrocarbon group having 9 to 19 carbon atoms which may have a hydroxyl group at the 1-position, which includes the steps of reacting an aminodiol represented by the following general formula (1):

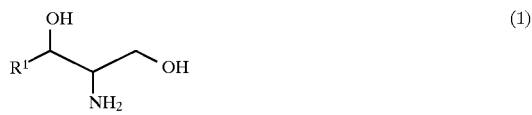

(1)

wherein $R^1$ is the same as $R^1$ in general formula (3) with a fatty acid alkyl ester represented by the following general formula (2):

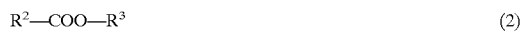

$R^2$—COO—$R^3$ (2)

wherein $R^2$ is the same as $R^2$ in general formula (3) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system.

18 Claims, No Drawings

METHOD OF MAKING PRIMARY AMIDE DERIVATIVE

BACKGROUND OF THE INVENTION

1. Field of the Invention

The present invention relates to novel methods of making primary amide derivatives. More particularly, the present invention relates to methods of making a primary amide derivative and an optically active primary amide derivative, which comprise reacting an aminodiol having a primary alcoholic hydroxyl group and a secondary alcoholic hydroxyl group with a fatty acid alkyl ester in an alcoholic solvent so as to selectively acylate only the amino group of the aminodiol.

2. Description of the Related Art

In conventional methods of making amide derivatives from aminoalcohol derivatives, the aminoalcohol derivatives are acylated with acid anhydrides, acyl halides, fatty acid esters, or fatty acids in the absence of a catalyst or in the presence of a basic catalyst such as sodium alkoxide, triethylamine, or pyridine. However, these methods are disadvantageous in that a stoichiometrically excess amount of base must be added to a raw aminodiol material, and a troublesome additional process is required for removing salt which is formed during the reaction.

On the other hand, a method for synthesizing a primary amide compound from a primary amine compound and fatty acid ester is disclosed by F. J. Edmund et al. in *J. Am. Oil Chem. Sos.*, 38, 600 (1961). This method requires distillation and drying of the solvent and reagents before use. When this method is applied to an aminodiol compound having both a primary alcoholic hydroxyl group and a secondary hydroxyl group, the primary alcoholic hydroxyl group is also acylated. This results in a decreased yield of the objective product. Furthermore, because hydrolysis for removing the ester by-product forms a large amount of a fatty acid salt, a troublesome additional step is needed to remove the resulting salt.

Japanese Unexamined Patent Publication No. 63-216,852 discloses N-acylation of secondary amines having a primary alcoholic hydroxyl group and a secondary alcoholic hydroxyl group with methyl esters of fatty acids, without a solvent and in the presence of a basic catalyst. The use of a catalytic amount of a polyether compound provides a more satisfactory result.

Japanese Unexamined Patent Publication No. 4-282,304 discloses a method of making a secondary amide compound by N- acylation of a secondary amine having a primary alcoholic hydroxyl group and a secondary alcoholic hydroxyl group with methyl esters of 2-hydroxyfatty acids and in the absence of a solvent.

However, according to tracing experiments conducted by the present inventors, the objective primary amide product cannot effectively form an aminodiol compound having a primary alcoholic hydroxyl group and a secondary alcoholic hydroxyl group by the above-mentioned conventional amidation process in the absence of a solvent or with a small amount of a polyether compound. More particularly, the primary amide derivative formed during the reaction is highly crystalline and has a higher melting point. Consequently, the crystallized derivative causes a decrease in stirring effect during the reaction and this in turn results in an incomplete reaction. Heating the reaction system in order to complete the reaction causes a side reaction due to esterification of the primary alcohol. Furthermore, because the cooled amide product is completely crystallized after the reaction, it is difficult to industrially remove the product from the reactor.

As set forth above, when aminodiols are N-acylated without a solvent, the resulting amide derivatives are crystallized and solidified as the reaction proceeds. Consequently, it is difficult to remove the products from the reactor. When using a solvent such as a polyether compound, crystallization also occurs during the reaction and the cooling step, and another solvent is required for removing the product from the reactor.

SUMMARY OF THE INVENTION

It is therefore an object of the present invention to provide a more efficient method of selectively N-acylating the amino group of an aminodiol having a primary alcoholic hydroxyl group and a secondary alcoholic hydroxyl group, where the product is not crystallized during the reaction and where an additional troublesome procedure is not needed for extracting and purifying the objective product after the reaction.

The present inventors investigated a method of making a primary amide derivative by N-acylating only the amino group of an aminodiol having a primary alcoholic hydroxyl group and a secondary alcoholic hydroxyl group using a solvent, and discovered that when using an alcohol as the solvent which does not crystallize at room temperature and which has a relatively high boiling point, the objective product is efficiently produced.

More particularly, the present invention has been achieved by providing a method of making a primary amide derivative represented by the following general formula (3):

wherein $R^1$ represents a linear saturated aliphatic hydrocarbon group having 11 to 19 carbon atoms, and $R^2$ represents a linear saturated or unsaturated aliphatic hydrocarbon group having 9 to 19 carbon atoms which may have a hydroxyl group at the 1-position, comprising: reacting an aminodiol represented by the following general formula (1):

wherein $R^1$ is the same as $R^1$ in general formula (3), with a fatty acid alkyl ester represented by the following general formula (2):

$$R^2\text{—COO—}R^3 \qquad (2)$$

wherein $R^2$ is the same as $R^2$ in general formula (3) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system.

In another embodiment, the present invention provides a method of making an optically active, primary amide derivative represented by the following general formula (5):

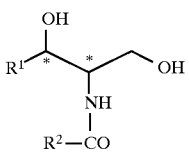

(5)

wherein $R^1$ represents a linear saturated aliphatic hydrocarbon group having 11 to 19 carbon atoms, $R^2$ represents a linear saturated or unsaturated aliphatic hydrocarbon group having 9 to 19 carbon atoms which may have a hydroxyl group at the 1-position, and the symbol * represents an asymmetric carbon atom, comprising:

reacting an optically active aminodiol represented by the following general formula (4):

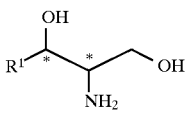

(4)

wherein $R^1$ and the symbol * are the same as $R^1$ and * in general formula (5), respectively, with a fatty acid alkyl ester represented by the following general formula (2):

$R^2\text{—COO—}R^3$ (2)

wherein $R^2$ is the same as $R^2$ in general formula (5) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system.

In accordance with a preferred embodiment of the present invention, the removing step comprises evacuating the lower alcohol formed during the reaction from the reaction system.

The method of the present invention is preferably used for preparing a (2S,3R)-2-acylamino-1,3-diol as an optically active primary amide derivative represented by general formula (5).

In the method of the present invention, when using an alcoholic solvent having a low solubility in water, a primary amide derivative can be produced in high yield by reacting an aminodiol having a primary alcoholic hydroxyl group and a secondary alcoholic hydroxyl group with a fatty acid alkyl ester in the presence of a basic catalyst, while removing the lower alcohol formed during the reaction from the reaction system.

Furthermore, because the objective primary amide derivative formed during the reaction can be recrystallized from the alcoholic solvent that is used in the reaction, the inventive method disperses with the need for an additional purifying operation.

DESCRIPTION OF THE PREFERRED EMBODIMENTS

The aminodiol starting material having a primary alcoholic hydroxyl group and a secondary alcoholic hydroxyl group represented by the general formula (1) as set forth above can be synthesized according to the method described, for example, in D. Shapiro et al., *J. Am. Chem. Soc.*, 80, 2170 (1958).

For example, in the synthesis of racemic 2-aminooctadecane-1,3-diol which is an aminodiol having 18 carbon atoms, the ester and ketone groups of a 2-acetamino-3-oxooctadecanoate ester are reduced with lithium aluminum hydride. The acetyl group is then removed to give a racemic 2-aminooctadecane-1,3-diol.

Furthermore, in preparing an optically active primary amide derivative represented by general formula (5) as set forth above, an optically active aminodiol represented by general formula (4) as another starting material can be synthesized according to the method described, for example, in Japanese Unexamined Patent Publication No. 6-80,617.

When the above 2-acetamino-3-oxooctadecanoate ester is used as a starting material (compound A in the following reaction scheme), the ester is converted to an optically active (2R, 3S)-2-acetamino-3-hydroxyoctadecanoate ester (compound B) by an asymmetric hydrogenation reaction using a ruthenium-optically active phosphine complex catalyst, the hydroxyl group of the ester is inverted with thionyl chloride to a (2R,3R)-isomer (compound C), and a natural-type optically active (2S,3R)-2-aminooctadecane-1,3-diol (compound D) is prepared by reducing the ester group and deacetylation.

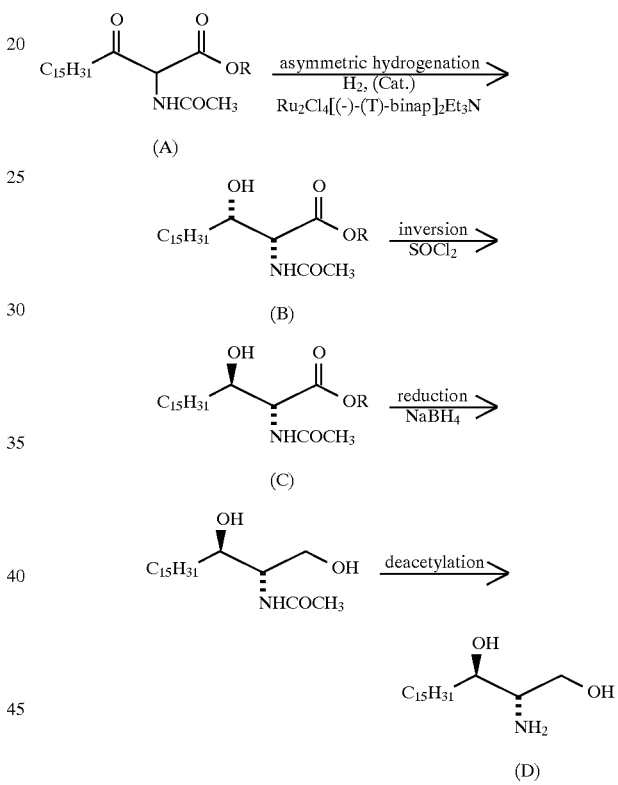

R in compounds A, B and C represents a lower alkyl group, and (T)-binap is 2,2'-bis(di-p-tolylphosphino-1,1'-binaphthyl If the hydroxyl group is not inverted, a (2S,3S)-isomer can be synthesized. In such manner, compounds having different steric configurations such as a (2R,3R)-isomer and a (2R,3S)-isomer can be prepared with various catalytic ligands, for example, a (+)—phosphine complex.

Examples of the fatty acid alkyl esters represented by the general formula (2):

$R^2\text{—COO—}R^3$ (2)

wherein $R^2$ represents a linear saturated or unsaturated aliphatic hydrocarbon group having 9 to 19 carbon atoms which may have a hydroxyl group at the 1-position and $R^3$ represents a lower alkyl group, include methyl and ethyl esters of fatty acids, e.g., methyl decanoate, ethyl decanoate, methyl undecanoate, ethyl undecanoate, methyl dodecanoate, ethyl dodecanoate, methyl tridecanoate, ethyl tridecanoate, methyl tetradecanoate, ethyl tetradecanoate, methyl pentadecanoate, ethyl pentadecanoate, methyl hexadecanoate, ethyl hexadecanoate, methyl cis-9-hexadecenoate, ethyl cis-9-hexadecenoate, methyl heptadecanoate, ethyl heptadecanoate, methyl octadecanoate, ethyl octadecanoate, methyl cis-9-octadecenoate, ethyl cis-9-octadecenoate, methyl cis,cis-9,12-octadecadienoate, ethyl cis,cis-9,12-octadecadienoate, methyl nonadecanoate, ethyl nonadecanoate, methyl eicosanoate and ethyl eicosanoate.

Examples of the fatty acid esters having a hydroxyl group at the 1-position of $R^2$, i.e., alkyl esters of 2-hydroxy fatty acids, include methyl 2-hydroxydecanoate, ethyl 2-hydroxydecanoate, methyl 2-hydroxyundecanoate, ethyl 2-hydroxyundecanoate, methyl 2-hydroxydodecanoate, ethyl 2-hydroxydodecanoate, methyl 2-hydroxytridecanoate, ethyl 2-hydroxytridecanoate, methyl 2-hydroxytetradecanoate, ethyl 2-hydroxytetradecanoate, methyl 2-hydroxypentadecanoate, ethyl 2-hydroxypentadecanoate, methyl 2-hydroxyhexadecanoate, ethyl 2-hydroxyhexadecanoate, methyl 2-hydroxyheptadecanoate, ethyl 2-hydroxyheptadecanoate, methyl 2-hydroxyoctadecanoate, ethyl 2-hydroxyoctadecanoate, methyl 2-hydroxynonadecanoate, ethyl 2-hydroxynonadecanoate, methyl 2-hydroxyeicosanoate and ethyl 2-hydroxyeicosanoate.

Among the lower alkyl groups of the esters are lower straight and branched alkyl groups having 1 to 4 carbon atoms, preferably methyl and ethyl groups.

In the method of the present invention, the lower alcohol ($R^3OH$) that is removed from the reaction system has a boiling point that is lower than that of the alcoholic solvent.

The fatty acid alkyl ester represented by general formula (2) is used in an amount of from 1 to 1.5 mols, and preferably from 1.1 to 1.5 mols, per 1 mol of the aminodiol represented by general formula (1) in the reaction of the present invention.

Examples of alcoholic solvents for use in the reaction system include alcohols having 3 to 8 carbon atoms, e.g., n-propyl alcohol, isopropyl alcohol, n-butylalcohol, isobutyl alcohol, amyl alcohol, hexyl alcohol, heptyl alcohol and octyl alcohol. These alcohols may be used alone or in combination. Among them, n-butyl alcohol is preferred because it can be easily evacuated from the reaction solution and is easily handled.

The alcoholic solvent may be used in an amount of from 5 to 10 fold by weight and preferably from 7 to 8 fold by weight, to the amount of the aminodiol represented by the general formula (1). If the amount of the alcoholic solvent is too low, a primary alcoholic hydroxyl group will be esterified. Because the esterified product is highly crystalline, it is difficult to remove the product from the reaction solution by recrystallization.

Examples of basic catalyst for use in the present invention include sodium hydroxide, potassium hydroxide and sodium alkoxides. The basic catalyst may be used in an amount of from 0.01 to 0.2 mol per 1 mol of the fatty acid alkyl ester represented by the general formula (2).

In the present invention, the fatty acid alkyl ester represented by general formula (2) is added dropwise to the reaction solution containing an aminodiol represented by general formula (1) or (4) and a basic catalyst over a period of from 15 to 30 minutes. Alternatively, the fatty acid alkyl ester may be added after heating the reaction solution for 30 minutes to 1 hour.

In the reaction of the present invention, the amino group of the aminodiol having a primary alcoholic hydroxyl group and a secondary alcoholic hydroxyl group is selectively and effectively N-acylated by removing the lower alcohol such as methanol or ethanol which is formed during the acylation from the reaction system. Thus, the reaction can proceed under reduced pressure (by evacuating or applying a vacuum to the reaction vessel) or in an inert gas atmosphere. For example, the reaction may be carried out under a reduced pressure of 30 to 100 mmHg at a temperature of 90° to 120° C. for 1 to 2 hours. Alternatively, the reaction may be carried out, for example, by passing a nitrogen stream of 20 ml/min. as an inert gas atmosphere through the reaction vessel at a temperature of 90° to 120° C. for approximately 1.5 hours.

After the reaction, the solution is removed from the reactor and cooled to a temperature within the range from room temperature to −10° C. to precipitate crude crystals of the objective primary amide derivative represented by general formula (3) or (5). After collecting the crude crystals, the crude crystals can be easily recrystallized with methanol, ethanol or acetonitrile for purification.

In the method of the present invention, a primary amide derivative can be produced in high yield by reacting an aminodiol having a primary alcoholic hydroxyl group and a secondary alcoholic hydroxyl group with a fatty acid alkyl ester in an alcoholic solvent and in the presence of a basic catalyst, while removing the lower alcohol formed during the reaction from the reaction system. Furthermore, the reaction is not accompanied by crystallization, and also dispenses with the need for troublesome extraction and purification operations after the reaction. The resulting primary amide derivative is useful for enhancing the water retention capacity of the skin, and is also useful as a base agent for cosmetics and the like.

EXAMPLES

The following Examples illustrate preferred embodiments of the present invention. However, the present invention should not be construed as being limited thereto. In the Examples, the following analytical instruments and materials were used for identifying the reaction products.

Analytical Instruments and Materials

High Performance Liquid Chromatograph Waters 510 (made by Waters, Ltd.) Detector: Waters 484 UV detector (made by Waters, Ltd.)

Nuclear Magnetic Resonance Spectrometer AM-400 (400 MHz: made by Bruker Inc.) Internal standard: tetramethylsilane Optical Rotation Measurement DIP-4 (made by JASCO Inc.)

Elemental Analyzer CHN-2400 (made by Perkin Elmer, Ltd.)

Mass Spectrometer M80B (made by Hitachi, Ltd.)

Example 1

Synthesis of 2-octadecanoylaminohexadecane-1,3-diol

Into a 100 ml four-neck flask equipped with a stirrer, dropping funnel and thermometer were placed 50 mg of commercially available 85% potassium hydroxide, 1.5 g (5 mmol) of 2-aminohexadecane-1,3-diol and 15 ml of butanol. The mixture was heated while stirring to 90° C. for 30 minutes. 2.24 g (7.5 mmol) of methyl stearate (methyl octadecanoate) in 5 ml of a butanol solution was then added dropwise while introducing nitrogen into the reaction system. After stirring at 90° C. for 2 hours, the product removed from the reactor was cooled and the resulting crystals were collected. The crude crystals were washed with methanol and dried. The yield of the resulting 2-octadecanoylaminohexadecane-1,3-diol was 87.2%.

Melting Point: 96.7° to 98.2° C.
$^1$H-NMR (CDCl$_3$:CD$_3$OD=10:1 δppm):
0.88 (6H, t, J=7.0 Hz),
1.27 (50H, brs), 1.54 (2H, m),
1.64 (2H, m), 2.23 (2H, t, J=7.6 Hz),
3.63 (1H, m),
3.68 (1H, d, d, J=3.3, 11.5 Hz),
3.80 (1H, m),
3.83 (1H, d, d, J=3.3, 11.5 Hz),
6.37 (1H, d, J=7.8 Hz)
MS: 540 (M$^+$+1)
Elemental Analysis (as C$_{34}$H$_{69}$NO$_3$):
Theoretical (%) C:75.64, H:12.88, N:2.59
Observed (%) C:75.60, H:12.78, N:2.66

Example 2

Synthesis of 2-hexadecanoylaminohexadecane-1,3-diol

Using the same procedure as in Example 1, 2-hexadecanoylaminohexadecane-1,3-diol was prepared from methyl palmitate (methyl hexadecanoate) and 2-aminohexadecane-1,3-diol. The yield was 89.3%.

Melting Point: 99.3 to 103.4° C.
$^1$H-NMR (CDCl$_3$:CD$_3$OD=10:1 δppm):
0.88 (6H, t, J=6.9 Hz),
1.27 (46H, brs), 1.54 (2H, m),
1.64 (2H, m), 2.22 (2H, t, J=7.8 Hz),
3.62 (1H, m),
3.68 (1H, d, d, J=3.4, 11.2 Hz),
3.79 (1H, m),
3.84 (1H, d, d, J=3.4, 11.2 Hz),
6.37 (1H, d, J=7.7 Hz)
MS: 512 (M$^+$+1)
Elemental Analysis (as C$_{32}$H$_{65}$NO$_3$):
Theoretical (%) C:75.09, H:12.80, N:2.74
Observed (%) C:75.12, H:12.70, N:2.69

Example 3

Synthesis of 2-linoleoylaminohexadecane-1,3-diol

Using the same procedure as in Example 1, 2-linoleoylaminohexadecane-1,3-diol was prepared from methyl linoleate (methyl cis,cis-9,12-octadecadienoate) and 2-aminooctadecane-1,3-diol. The yield was 86.1%.

Melting Point: 92° to 99.5° C.
$^1$H-NMR (CDCl$_3$:CD$_3$OD=10:1 δppm):
0.88 (6H, t, J=7.0 Hz),
1.27 (48H, brs), 1.54 (2H, m),
1.64 (2H, m),
2.23 (2H, t, J=7.8 Hz),
3.76 (1H, d, d, J=3.5, 11.3 Hz),
3.78 (1H, m),
4.01 (1H, d, d, J=3.5, 11.3 Hz),
5.34 (4H, m),
6.37 (1H, d, J=7.8 Hz)
MS: 564 (M$^+$+1)
Elemental Analysis (as C$_{36}$H$_{69}$NO$_3$):
Theoretical (%) C:76.67, H:12.33, N:2.48
Observed (%) C:76.74, H:12.38, N:2.49

Example 4

Synthesis of (2S,3R)-2-octadecanoylaminooctadecane-1,3-diol

Into a 100 ml four-neck flask equipped with a stirrer, dropping funnel and thermometer were placed 50 mg of commercially available 85% potassium hydroxide, 1.5 g (5 mmol) of (2S,3R)-2-aminooctadecane-1,3-diol and 15 ml of butanol. The mixture was heated while stirring to 90° C. for 30 minutes. 2.24 g (7.5 mmol) of methyl stearate (methyl octadecanoate) in 5 ml of a butanol solution was then dropwise added while introducing nitrogen into the reaction system. After stirring at 90° C. for 2 hours, the product removed from the reactor was cooled and the resulting crystals were collected. The crude crystals were recrystallized from methanol and dried. The yield of the resulting (2S,3R)-2-octadecanoylaminooctadecane-1,3-diol was 82.4% (2.3 g).

Melting Point: 105° to 106° C.
Optical Rotation: $[\alpha]^{25}_D$+3.97°
(c=0.13, CHCl$_3$:CH$_3$OH=10:1)
$^1$H-NMR (CDCl$_3$:CD$_3$OD=10:1 δppm):
0.88 (6H, t, J=7.0 Hz),
1.27 (54H, brs), 1.54 (2H, m),
1.64 (2H, m), 2.23 (2H, t, J=7.8 Hz),
3.76 (1H, d, d, J=3.3, 11.5 Hz),
3.78 (1H, m),
4.02 (1H, d, d, J=3.3, 11.5 Hz),
6.38 (1H, d, J=7.8 Hz)
MS: 568 (M$^+$+1)
Elemental Analysis (as C$_{36}$H$_{73}$NO$_3$):
Theoretical (%) C:76.13, H:12.95, N:2.47
Observed (%) C:76.04, H:12.90, N:2.51

Example 5

Synthesis of (2S,3R)-2-tetradecanoylaminooctadecane-1,3-diol

Using the same procedure as in Example 4, (2S,3R)-2-tetradecanoylaminooctadecane-1,3-diol was prepared from methyl myristate (methyl tetradecanoate) and (2S,3R)-2-aminooctadecane-1,3-diol. The yield was 87.1%.

Melting Point: 101° to 103° C.
Optical Rotation: $[\alpha]^{25}_D$+3.27°
(c=0.122, CHCl$_3$:CH$_3$OH=10:1)
$^1$H-NMR (CDCl$_3$:CD$_3$OD=10:1 δpm):
0.88 (6H, t, J=7.0 Hz),
1.27 (48H, brs), 1.54 (2H, m),
1.64 (2H, m),
2.23 (2H, d, d, J=7.4, 7.8 Hz),
3.76 (1H, d, d, J=3.5, 11.5 Hz),
3.78 (1H, m),
4.01 (1H, d, d, J=3.5, 11.5 Hz),
6.37 (1H, d, J=7.8 Hz)
MS: 512 (M$^+$+1)
Elemental Analysis (as C$_{32}$H$_{65}$NO$_3$):
Theoretical (%) C:75.09, H:12.80, N:2.74
Observed (%) C:75.15, H:12.70, N:2.69

Example 6

Synthesis of (2S,3R)-2-hexadecanoylaminooctadecane-1,3-diol

Using the same procedure as in Example 4, (2S,3R)-2-hexadecanoylaminooctadecane-1,3-diol was prepared from methyl palmitate (methyl hexadecanoate) and (2S,3R)-2-aminooctadecane-1,3-diol. The yield was 85.7%.

Melting Point: 105.5° to 106.7° C.
Optical Rotation: $[\alpha]^{25}_D$+3.94°
(c=0.12, CHCl$_3$:CH$_3$OH=10:1)
$^1$H-NMR (CDCl$_3$:CD$_3$OD=10:1 δppm):
0.88 (6H, t, J=7.0 Hz),
1.27 (52H, brs), 1.54 (2H, m),
1.64 (2H, m),
2.23 (2H, t, J=7.8 Hz),
3.76 (1H, d, d, J=3.5, 11.5 Hz),
3.78 (1H, m),
4.01 (1H, d, d, J=3.3, 11.5 Hz),
6.37 (1H, d, J=7.8 Hz)
MS: 540 (M$^+$+1)
Elemental Analysis (as C$_{34}$H$_{69}$NO$_3$):
Theoretical (%) C:76.64, H:12.88, N:2.59
Observed (%) C:76.68, H:12.90, N:2.49

Example 7

Synthesis of (2S,3R)-2-oleoylaminooctadecane-1,3-diol

Using the same procedure as in Example 4, (2S,3R)-2-oleoylaminooctadecane-1,3-diol was prepared from methyl oleate (methyl cis-9-octadecenoate) and (2S,3R)-2-aminooctadecane-1,3-diol. The yield was 86.5%.

Melting Point: 96.5° to 99.5° C.
Optical Rotation: $[\alpha]^{25}_D$+3.25°
(c=0.3, CHCl$_3$:CH$_3$OH=10:1)
$^1$H-NMR (CDCl$_3$:CD$_3$OD=10:1 δppm):
0.88 (6H, t, J=7.0 Hz),
1.27 (48H, brs), 1.54 (2H, m),
1.64 (2H, m), 2.00(4H,m),
2.23 (2H, t, J=7.8 Hz),
3.76 (1H, d, d, J=3.3, 11.5 Hz),
3.78 (1H, m),
4.01 (1H, d, d, J=3.5, 11.5 Hz),
5.34 (2H, m),
6.94 (1H, d, J=8.2 Hz)
MS: 566 (M$^+$+1)

Example 8

Synthesis of (2S,3R,2'RS)-2-(2'hydroxydecanoyl)aminooctadecane-1,3-diol

Using the same procedure as in Example 4, (2S,3R,2'RS)-2-(2'-hydroydecanyoyl) aminooctadecane-1,3-diol was prepared from methyl 2-hydroxydecanoate and (2S,3R)-2-aminooctadecane-1,3-diol. The yield was 90.5%.

Melting Point: 89° to 92° C.
$^1$H-NMR (CDCl$_3$:CD$_3$OD=10:1 δppm):
0.86 (3H, t, J=7.0 Hz),
0.88 (3H, t, J=7.0 Hz),
1.27 (38H, brs), 1.64 (2H, m),
2.30 (1H, d, d, J=9.3, 15.0 Hz),
2.43 (1H, d, d, J=2.7, 15.0 Hz),
2.50 (1H, d, J=6.9 Hz),
2.62 (1H, br), 3.44 (2H, br),
3.80 (lH,m),
4.01 (1H, d, d, J=3.0, 9.3 Hz),
6.60 (1H, d, J=6.9 Hz)
MS: 471 (M$^+$+1)
Elemental Analysis (as C$_{28}$H$_{57}$NO$_4$):
Theoretical (%) C:71.28, H:12.18, N:2.97
Observed (%) C:71.35, H:12.20, N:2.95

Example 9

Synthesis of (2S,3R,2'RS)-2-(2'-hydroxyhexadecanoyl)-aminooctadecane-1,3-diol

Using the same procedure as in Example 4, (2S,3R,2'RS) -2-(2'-hydroxyhexadecanoyl) aminooctadecane-1,3-diol was prepared from methyl 2-hydroxyhexadecanoate and (2S,3R)-2-aminooctdecane-1,3-diol. The yield was 90.%.

Melting Point: 112° to 122° C.
$^1$H-NMR (CDCl$_3$:CD$_3$OD=10:1 δppm):
0.86 (3H, t, J=7.0 Hz),
0.88 (3H, t, J=7.0 Hz),
1.27 (50H, brs), 1.64 (2H, m),
2.30 (1H, d, d, J=9.3, 15.0 Hz),
2.43 (1H, d, d, J=2.7, 15.0 Hz),
2.50 (1H, d, J=6.9 Hz),
2.62 (1H, br), 3.44 (2H, br),
3.80 (lH,m),
4.01 (1H, d, d, J=3.0, 9.3 Hz),
6.60 (1H, d, J=6.9 Hz)
MS: 556 (M$^+$+1)
Elemental Analysis (as C$_{34}$H$_{69}$NO$_4$):
Theoretical (%) C:73.46, H:12.51, N:2.52
Observed (%) C:73.35, H:12.40, N:2.49

In the following Comparative Examples, tracing experiments were carried out following the method described in Japanese Unexamined Patent Publication No. 63-216,852.

Comparative Example 1

Synthesis of (2S,3R)-2-octadecanoylaminooctadecane-1,3-diol

Into a 100 ml four-neck flask equipped with a stirrer, dropping funnel and thermometer were placed 50 mg of commercially available 85% potassium hydroxide and 1.5 g (5 mmol) of (2S,3R)-2-aminooctadecane-1,3-diol. The mixture was heated while stirring to 90° C. for 30 minutes. While introducing nitrogen into the reaction system, 2.24 g (7.5 mmol) of methyl stearate (methyl octadecanoate) was then added dropwise. After a period of 30 minutes, stirring was stopped due to precipitation of a crystalline product. Ethanol was added to the reactor to recrystallize the product. The yield of the resulting (2S,3R)-2-octadecanoylaminooctadecane-1,3-diol was 56% (1.59 g).

Comparative Example 2

Synthesis of (2S,3R)-2-octadecanoylaminooctadecane-1,3-diol

Into a 100 ml four-neck flask equipped with a stirrer, dropping funnel and thermometer were placed 50 mg of commercially available 85% potassium hydroxide and 1.5 g (5 mmol) of (2S,3R)-2-aminooctadecane-1,3-diol. The mixture was then heated to 90° C. while stirring for 30 minutes.

While introducing nitrogen into the reaction system, 2.24 g (7.5 mmol) of methyl stearate (methyl octadecanoate) was then added dropwise. Stirring was stopped after a period of 30 minutes due to precipitation of a crystalline product, and the contents were then heated to 120° C. The heated product was collected without cooling. The product was recrystallized with methanol. This product (2.04 g) was a mixture of (2S,3R)-2-octadecanoylaminooctadecane-1,3-diol and (2S,3R)-3-hydroxy-2-octadecanoylamino-1-octadecanoyloxyoctadecane, which compounds were not separable by recrystallization.

Comparative Example 3

Synthesis of (2S,3R)-2-octadecanoylaminooctadecane-1,3-diol

Into a 100 ml four-neck flask equipped with a stirrer, dropping funnel and thermometer were placed 50 mg of commercially available 85% potassium hydroxide and 1.5 g (5 mmol) of (2S,3R)-2-aminooctadecane-1,3-diol. The mixture was heated to 90° C. with stirring for 30 minutes. While introducing nitrogen into the reaction system, 2.24 g (7.5 mmol) of methyl stearate (methyl octadecanoate) was then added dropwise. Stirring was stopped after a period of 30 minutes due to precipitation of a crystalline product, and the contents were heated at 120° C. for 2 hours to continue the reaction. The heated product was collected without cooling. The product was recrystallized with ethanol. This product (2.34 g) was a mixture of (2S,3R)-2-octadecanoylamino-octadecane-1,3-diol, (2S,3R)-3-hydroxy-2-octadecanoylamino-1-octadecanoyloxoctadecane and other unidentified compounds which could not be separated from one another.

As set forth above, a solvent was not used in Comparative Example 1. Consequently, the reaction was incomplete due to crystalline precipitation and the yield was unsatisfactorily low. When the reaction conditions were modified so that the crystals did not precipitate (Comparative Examples 2 and 3), the resulting products were mixtures containing the objective product and other compounds. However, the desired products could not be isolated from the respective mixtures.

While the invention has been described in detail and with reference to specific embodiments thereof, it will be apparent to one skilled in the art that various changes and modifications can be made therein without departing from the spirit and scope thereof.

What is claimed is:

1. A method of making a primary amide derivative represented by the following general formula (3):

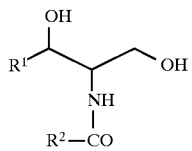

(3)

wherein $R^1$ represents a linear saturated aliphatic hydrocarbon group having 11 to 19 carbon atoms, and $R^2$ represents a linear saturated or unsaturated aliphatic hydrocarbon group having 9 to 19 carbon atoms which may have a hydroxyl group at the 1-position, comprising:

reacting an aminodiol represented by the following general formula (1):

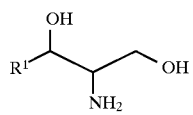

(1)

wherein $R^1$ is the same as R1 in general formula (3), with a fatty acid alkyl ester represented by the following general formula (2):

$R^2$—COO—$R^3$ (2)

wherein $R^2$ is the same as $R^2$ in general formula (3) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system;

wherein said removing step comprises removing said lower alcohol by carrying out the reaction under a reduced pressure of from 30 to 100 mmHg at a temperature of from 90° to 120° C.

2. A method of making an optically active, primary amide derivative represented by the following general formula (5):

(5)

wherein $R^1$ represents a linear saturated aliphatic hydrocarbon group having 11 to 19 carbon atoms, $R^2$ represents a linear saturated or unsaturated aliphatic hydrocarbon group having 9 to 19 carbon atoms which may have a hydroxyl group at the 1-position, and the symbol * represents an asymmetric carbon atom, comprising:

reacting an optically active aminodiol represented by the following general formula (4):

(4)

wherein $R^1$ is the same as $R^1$ in general formula (5), with a fatty acid alkyl ester represented by the following general formula (2):

$R^2$—COO—$R^3$ (2)

wherein $R^2$ is the same as $R^2$ in general formula (5) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system;

wherein said removing step comprises removing said lower alcohol by carrying out the reaction under a reduced pressure of from 30 to 100 mmHg at a temperature of from 90° to 120° C.

3. A method of making a primary amide derivative represented by the following general formula (3):

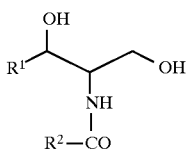

wherein $R^1$ represents a linear saturated aliphatic hydrocarbon group having 11 to 19 carbon atoms, and $R^2$ represents a linear saturated or unsaturated aliphatic hydrocarbon group having 9 to 19 carbon atoms which may have a hydroxyl group at the 1-position, comprising:

reacting an aminodiol represented by the following general formula (1):

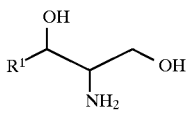

wherein $R^1$ is the same as $R^1$ in general formula (3), with a fatty acid alkyl ester represented by the following general formula (2):

wherein $R^2$ is the same as $R^2$ in general formula (3) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system;

wherein said removing step comprises removing said lower alcohol by carrying out the reaction in an inert gas atmosphere at a temperature of from 90° to 120° C.

4. A method of making an optically active, primary amide derivative represented by the following general formula (5):

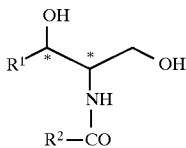

wherein $R^1$ represents a linear saturated aliphatic hydrocarbon group having 11 to 19 carbon atoms, $R^2$ represents a linear saturated or unsaturated aliphatic hydrocarbon group having 9 to 19 carbon atoms which may have a hydroxyl group at the 1-position, and the symbol * represents an asymmetric carbon atom, comprising:

reacting an optically active aminodiol represented by the following general formula (4):

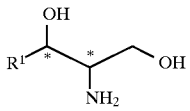

wherein $R^1$ is the same as $R^1$ in general formula (5), with a fatty acid alkyl ester represented by the following general formula (2):

wherein $R^2$ is the same as $R^2$ in general formula (5) and $R^3$ represents a lower alkyl group, in a reaction system comprising an alcoholic solvent and in the presence of a basic catalyst, said reacting step forming a lower alcohol as a by-product; and removing the lower alcohol formed during the reaction from the reaction system;

wherein said removing step comprises removing said lower alcohol by carrying out the reaction in an inert gas atmosphere at a temperature of from 90° to 120° C.

5. The method of making a primary amide derivative according to claim 1 or 3, wherein said alcoholic solvent is an alcohol having from 3 to 8 carbon atoms.

6. The method of making an optically active, primary amide derivative according to claim 2 or 4, wherein said alcoholic solvent is an alcohol having from 3 to 8 carbon atoms.

7. The method of making a primary amide derivative according to claim 1 or 3, wherein said alcoholic solvent is n-butanol.

8. The method of making an optically active, primary amide derivative according to claim 2 or 4, wherein said alcoholic solvent is n-butanol.

9. The method of making an optically active, primary amide derivative according to claim 2 or 3, wherein said optically active primary amide derivative has a steric (2S, 3R)-configuration.

10. The method of making a primary amide derivative according to claim 1 or 3, wherein the lower alkyl group represented by $R^3$ is methyl or ethyl.

11. The method of making a primary amide derivative according to claim 1 or 3, wherein the fatty acid alkyl ester represented by general formula (2) is used in an amount of from 1 to 1.5 mols per mol of the aminodiol represented by general formula (1).

12. The method of making a primary amide derivative according to claim 1 or 3, wherein the alcoholic solvent is used in an amount by weight of from 5 to 10 times the amount by weight of the aminodiol represented by general formula (1).

13. The method of making a primary amide derivative according to claim 1 or 3, wherein the basic catalyst is used in an amount of from 0.01 to 0.2 mol per mol of the fatty acid alkyl ester represented by general formula (2).

14. The method of making a primary amide derivative according to claim 1 or 3, further comprising the step of recovering a primary amide represented by general formula (3) from the reaction system.

15. The method of making of making an optically active, primary amide according to claim 2 or 4, wherein the lower alkyl group represented by $R^3$ is methyl or ethyl.

16. The method of making an optically active, primary amide according to claim 2 or 4, wherein the fatty acid alkyl ester represented by general formula (2) is used in an amount of from 1 to 1.5 mols per mol of the aminodiol represented by general formula (1).

17. The method of making an optically active, primary amide derivative according to claim 2 or 4, wherein the alcoholic solvent is used in an amount by weight of from 5 to 10 times the amount by weight of the aminodiol represented by general formula (1).

18. The method of making an optically active, primary amide derivative according to claim 2 or 4, wherein the basic catalyst is used in an amoun t of from 0.01 to 0.2 mol per mol of the fatty acid alkyl ester represented by general formula (2).

* * * * *